United States Patent
Forney et al.

(10) Patent No.: US 11,523,611 B2
(45) Date of Patent: Dec. 13, 2022

(54) METHODS OF INCREASING ALMOND YIELD

(71) Applicant: Valent U.S.A. LLC, San Ramon, CA (US)

(72) Inventors: Kevin Dale Forney, Bakersfield, CA (US); Peter Petracek, Grayslake, IL (US); Gabriel Munhoz Pedroso, Sao Paolo (BR)

(73) Assignee: VALENT U.S.A., LLC, San Ramon, CA (US)

( * ) Notice: Subject to any disclaimer, the term of this patent is extended or adjusted under 35 U.S.C. 154(b) by 0 days.

(21) Appl. No.: 17/365,192

(22) Filed: Jul. 1, 2021

(65) Prior Publication Data

US 2022/0000111 A1    Jan. 6, 2022

Related U.S. Application Data

(60) Provisional application No. 63/046,837, filed on Jul. 1, 2020.

(51) Int. Cl.
| | | |
|---|---|---|
| *A01H 3/04* | (2006.01) | |
| *A01N 43/40* | (2006.01) | |
| *A01H 6/74* | (2018.01) | |
| *A01N 37/44* | (2006.01) | |

(52) U.S. Cl.
CPC .............. *A01N 43/40* (2013.01); *A01H 3/04* (2013.01); *A01H 6/7427* (2018.05); *A01N 37/44* (2013.01)

(58) Field of Classification Search
CPC ................................ A01H 3/04; A01H 6/7427
See application file for complete search history.

(56) References Cited

FOREIGN PATENT DOCUMENTS

EP    0 938 468 B1 *  9/1997

OTHER PUBLICATIONS https://www.youtube.com/watch?v=SRslcobA5n4; "ReTain plant growth regulator for California" Retrieved from the Internet Sep. 28, 2021. (3 pages total).*

US EPA, Pesticide Label, RETAIN, Feb. 11, 2015; Retrieved from the Internet on Oct. 28, 2021; https://www3.epa.gov/pesticides/chem_search/ppls/073049-00058-20150211.pdf.*

Bee Culture—"Catch the Buzz—New Plant growth Regulator Labeled for Almonds in Bloom," Nov. 18, 2016; http://beekeepingtodayppodcast.com/. Retrieved from the Internet on Sep. 28, 2021.*

Rath et al., Yield increase and higher flesh firmness of 'Artic Snow' nectarine both at harvest in Australia and after export to Taiwan following pre-harvest application of ReTain Plant Growth Regulator (aminoethoxyvinylglycine, AVG), Australian Journal of Experimental Agriculture, 2004, 44, pp. 343-351.*

"RWJ Barnabas Health, The Skinny on Stone Fruits" (https://www.rwjbh.org/blog/2019/may/the-skinny-on-stone-fruits/; Retrieved from the Internet on Nov. 8, 2021).* https://www.merriam-webster.com/words-at-play/fruit-parts-words-and-their-origins#:~:text=At%20the%20center%20of%20fruit,pip%20encapsulated%20by%20the%20endocarp. Retrieved from the Internet on May 24, 2022.*

Fritts et al., Field efficacy of aminoethoxyvinylglycine (ReTain) far improving fruit set of almond. Conference paper: Proceedings of the 42nd Annual Meeting of the Plant Growth Regulation Society of America, Kona, Hawaii, USA, Jul. 19-23, 2015, pp. 83-92 ref.6 [online]. [Retrieved on Sep. 26, 2021). Retrieved from the internet <URL: https://www.cabdirect.org/cabdirect/abstract/20173267912> Abstract.

Wood, Influence of Aminoethoxyvinylglycine (AVG) on Yield and Quality of Nut Crops from a Commercial Pecan Orchard. Hortscience, 2011, vol. 46, No. 4, p. 586-589. Abstract; p. 587, col. 1, para 2-3: p. 588, col. 2, para 1.

United States Environmental Protection Agency Master Label ReTain(R), published Jul. 2015.

Lanoha Nurseries downloaded on May 31, 2022 from https://lanohanurseries.com/wp-content/uploads/2014/06/LanohaNurseries-Tree-Care-Fruit-tree-Schedule.pdf.

* cited by examiner

*Primary Examiner* — Susan McCormick Ewoldt
(74) *Attorney, Agent, or Firm* — Wood, Phillips, Katz, Clark & Mortimer

(57) ABSTRACT

The present invention is directed to a method of increasing almond nutmeat yield comprising applying aminoethoxyvinylglycine (AVG) or a salt of AVG at an effective rate to an almond tree following full bloom.

14 Claims, No Drawings

METHODS OF INCREASING ALMOND YIELD

FIELD OF THE INVENTION

The present invention is directed to a method of increasing almond nutmeat yield comprising applying aminoethoxyvinylglycine (AVG) or a salt thereof at an effective rate to an almond tree following full bloom.

BACKGROUND OF THE INVENTION

Aminoethoxyvinylglycine ("AVG"; also known as ([S]-trans-2-amino-4-(2-aminoethoxy)-3-butenoic acid and aviglycine) is a known ethylene antagonist. AVG formulations (such as those available from Valent BioSciences LLC, Libertyville, Ill.) have been shown to inhibit fruit drop and retain stone fruit and apple fruit quality (Silverman, et al., 2004. Plant Growth Reg. 43:153-161), increase cherry and walnut fruit set (Retamales and Petracek, 2010. Acta Hort. 884:337-341) and increase male flower number in cucurbits.

AVG-HCl is marketed under the tradename ReTain® (ReTain is a registered trademark of and available from Valent BioSciences LLC) for many uses including increasing nut set of almonds. However, the use of ReTain® on almonds commonly results in an increase in the kernel doubling (i.e. two nut kernels per shell). Kernel doubling is considered a quality defect in almonds, which results in a decreased crop value.

Accordingly, there is a need in the art for methods of treating almonds with AVG that does not result in a significant increase in kernel doubling.

SUMMARY OF THE INVENTION

The present invention is directed to a method of increasing almond nutmeat yield comprising applying aminoethoxyvinylglycine ("AVG") or a salt thereof at an effective rate to an almond tree following full bloom.

DETAILED DESCRIPTION OF THE INVENTION

The ReTain® specimen label instructs growers to apply ReTain® between 10% bloom and full bloom. The ReTain® label further instructs that application to almond trees either pre-bloom or after full bloom will reduce the efficacy of the treatment and that ReTain® should not be applied after petal fall. The ReTain® label notes that application of aminoethoxyvinylglycine ("AVG") to almond trees results in an increase kernel doubling. Applicant has unexpectedly discovered that application of AVG to almond trees after full bloom resulted in an increase in nutmeat yield without a corresponding increase in kernel doubling.

In one embodiment, the present invention is directed to a method of increasing almond nutmeat yield comprising applying AVG or a salt thereof at an effective rate to an almond tree following full bloom.

As used herein "salts" refers to those salts which retain the biological effectiveness and properties of the parent compounds and which are not biologically or otherwise harmful at the rates administered. Salts of AVG may be prepared from inorganic or organic acids or bases. In a preferred embodiment, the AVG is in the form of a chloride salt, more preferably AVG hydrochloride.

In a preferred embodiment, the AVG or salt thereof may be applied at a rate from about 1 to about 1 to about 1,000 grams per hectare, more preferably from about 1 to about 250 grams per hectare, even more preferably from about 60 to about 160 grams per hectare, even more preferably from about 62 to about 124 grams per hectare and most preferably at about 62 or about 124 grams per hectare.

In another preferred embodiment, the AVG or salt thereof may be applied from about 2 to about 7 weeks following full bloom, more preferably from about 6 to about 7 weeks following full bloom or in a combination of from about 3 to about 4 weeks following full bloom and from about 6 to about 7 weeks following full bloom.

In another preferred embodiment, the AVG or salt thereof may be applied one or more times and more preferably once or twice.

In another preferred embodiment, the AVG or salt thereof is applied prior to nut drop.

The methods of the present invention include application of AVG or salt thereof by any convenient means. Those skilled in the art are familiar with the modes of application that include foliar applications such as spraying, back-pack sprayer, thermo-fog, chemigation (a process of applying the composition through the irrigation system), by granular application, trunk injection or by impregnating the composition on fertilizer. Applications may be applied using either aerial or ground equipment.

In another embodiment, the AVG or salt thereof may be formulated with one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and preservatives, or slow release formulations.

As used herein, "effective rate" refers to an application rate of AVG capable of increasing almond nutmeat yield.

As used herein, "full bloom" refers to a period in the almond tree's bloom cycle in which at least 50% of the flower buds have reached anthesis.

As used herein, "nut drop" refers to a period in the almond trees nut production in which the majority of nuts begin to fall from the tree with or without agitation.

As used herein, "nutmeat" refers to the mature kernel of the almond nut.

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%. For example, the phrase "about 60 grams per hectare" is to be understood as "from 54 to 66 grams per hectare." Therefore, amounts within 10% of the claimed values are encompassed by the scope of the claims.

These representative embodiments are in no way limiting and are described solely to illustrate some aspects of the invention.

Further, the following example is offered by way of illustration only and not by way of limitation.

EXAMPLES

Example 1—Increase in Nutmeat of Almonds Following Post-Bloom AVG Application Method 6 sets of AVG applications were performed over a 2-year period. Each set of applications included a set of untreated control ("UTC") trees. For the two sets of applications performed during the 2018 calendar year AVG-HCl was applied to almond trees either between 10% and full bloom (i.e. bloom) or between 6-7 weeks following full bloom (i.e. post-bloom). For the three sets of applications performed during the 2019 calendar year an additional application was performed as follows: 3-4 weeks post-bloom in combination with 6-7 weeks post-bloom. Application occurred via a foliar spray at the rates indicated in Tables 1 and 2, below. Table 1, below, demonstrates the yield at harvest of almond nutmeat in kilograms per hectare. Table 2, below, demonstrates the percentage of shells harvested that contained two nut kernels.

TABLE 1

| Timing of App. | # of App. | Rate/App (g/Ha) | 2018-1 | 2018-1 | 2019-1 | 2019-2 | 2019-3 | Average |
|---|---|---|---|---|---|---|---|---|
| UTC | — | 0 | 635 | 1104 b | 1086 | 1163 b | 621 c | 922 b |
| Bloom | 1 | 124 | 712 | 1148 b | 1204 | 1198 b | 1031 a | 1068 ab |
| 6-7 weeks Post-bloom | 1 | 124 | 721 | 1345 a | 1168 | 1220 b | 713 bc | 1033 ab |
| 3-4 weeks Post-bloom & 6-7 weeks Post-bloom | 2 | 62 | — | — | 1164 | 1698 a | 825 b | 1229 a |

TABLE 2

| Timing of App. | # of App. | Rate/App (g/Ha) | 2018-1 | 2018-1 | 2019-1 | 2019-2 | 2019-3 | Average |
|---|---|---|---|---|---|---|---|---|
| UTC | — | 0 | — | 12.2 b | 1.5 b | 0.75 c | 0.3 c | 1.94 b |
| Bloom | 1 | 124 | — | 27.7 a | 3.5 a | 2.92 ab | 15.9 a | 8.62 a |
| 6-7 weeks Post-bloom | 1 | 124 | — | 6.6 b | 2.5 ab | 1.08 bc | 0.7 bc | 2.11 b |
| 3-4 weeks Post-bloom & 6-7 weeks Post-bloom | 2 | 62 | — | — | 1.3 b | 1.5 abc | 1.9 b | 1.55 b |

Results

As seen in Table 1, above, the application of AVG to almond trees during bloom increases nutmeat yield over untreated control. Unexpectedly, treating almond trees with AVG post-bloom resulted in a greater increase in nutmeat yield than that obtained when treating during bloom. This greater increase is unexpected as the specimen label for AVG use on almonds states that application after full bloom will reduce the efficacy of the treatment. Further, as seen in Table 2, treating almond trees during bloom results in a statistically significant increase in kernel doubling. Surprisingly, treating almond trees with AVG post-bloom did not result in a statistically significant increase in kernel doubling.

Example 2—Increase in Nutmeat of Almonds Following Post-Bloom AVG Application Method 2 sets of AVG applications were performed on 2 varieties of almonds, nonpareil and carmel. For the two sets of applications performed AVG-HCl was applied to almond trees either at full bloom or after full bloom, specifically at 22, 26, 29 or 33 days after full bloom ("DAFB"). Application occurred via a foliar spray at the rates indicated in Tables 3 and 4, below. Table 3, below, demonstrates the yield at harvest of nonpareil almonds in nuts per tree, nutmeat yield in kilograms per tree and percentage of double kernels. Table 4, below, demonstrates the same yield data for the carmel variety.

TABLE 3

| Timing of App. | Rate/App (g/Ha) | Nuts/ Tree | Nutmeat Yield (kg/tree) | % Kernel Doubling |
|---|---|---|---|---|
| UTC | 0 | 6946 ab | 7.01 b | 0.2 b |
| Full Bloom | 124 | 8153 ab | 8.03 ab | 3.8 a |
| 29 DAFB | 124 | 8435 a | 8.64 a | 1.4 b |
| 33 DAFB | 124 | 8350 a | 7.89 ab | 0.4 b |

TABLE 4

| Timing of App. | Rate/App (g/Ha) | Nuts/ Tree | Nutmeat Yield (kg/tree) | % Kernel Doubling |
|---|---|---|---|---|
| UTC | 0 | 7820 b | 6.76 | 5.5 bc |
| Full Bloom | 124 | 7039 b | 7.04 | 7.6 a |
| 22 DAFB | 124 | 8499 b | 7.94 | 5.6 bc |
| 26 DAFB | 124 | 9676 a | 8.50 | 3.7 c |

As demonstrated in Tables 3 and 4, above, treating almond trees during bloom or following full bloom with AVG increases nutmeat yield. Further, treating almond trees during bloom results in a statistically significant increase in kernel doubling. Surprisingly, treating almond trees with AVG post-bloom did not result in a statistically significant increase in kernel doubling.

Example 3—Increase in Nutmeat of Almonds Following Post-Bloom AVG Application Method 2 sets of AVG applications were performed on 2 varieties of almonds, nonpareil and carmel. For the two sets of applications performed AVG-HCl was applied to almond trees either at full bloom or after full bloom, specifically 15, 22, 26, 32, 36 or 38 DAFB. Application occurred via a foliar spray at the rates indicated in Tables 5 and 6, below. Table 5, below, demonstrates the yield at harvest of nonpareil almonds in nuts per tree, nut weight in kilograms per tree with or without shells and nut only and percentage of double kernels. Table 6, below, demonstrates the same yield data for the carmel variety.

TABLE 5

| Timing of App. | Rate/App (g/Ha) | Nuts/ Tree | Nutmeat Yield (kg/tree) | % Kernel Doubling |
|---|---|---|---|---|
| UTC | 0 | 6256.4 | 4.5 | 0.8 b |
| Full Bloom | 124 | 5251.6 | 4.3 | 2.0 a |
| 26 DAFB | 124 | 7636.8 | 5.9 | 0.8 b |
| 36 DAFB | 124 | 7789.8 | 6 | 0.6 c |

TABLE 6

| Timing of App. | Rate/App (g/Ha) | Nuts/ Tree | Nutmeat Yield (kg/tree) | % Kernel Doubling |
|---|---|---|---|---|
| UTC | 0 | 6808 | 5.20 | 0.4 b |
| Full Bloom | 124 | 7097 | 6.10 | 8.4 a |
| 15 DAFB | 124 | 7271 | 6.00 | 0.4 b |
| 22 DAFB | 124 | 7427 | 5.40 | 1.4 b |
| 32 DAFB | 124 | 6972 | 5.30 | 0.6 b |
| 38 DAFB | 124 | 8875 | 7.00 | 1 b |

As demonstrated in Tables 5 and 6, above, treating almond trees during bloom or following full bloom with AVG increases nutmeat yield. Further, treating almond trees during bloom results in a statistically significant increase in kernel doubling. Surprisingly, treating almond trees with AVG post-bloom did not result in a statistically significant increase in kernel doubling.

Example 4—Increase in Nutmeat of Almonds Following Post-Bloom AVG Application Method 2 sets of AVG applications were performed on nonpareil almonds at Newman, Calif. and Sutter, Calif. in 2020. Each set of applications included a set of untreated control ("UTC") trees. AVG-HCl was applied to almond trees either at 50% bloom (i.e. bloom), shuck split, or 7 days following shuck split. Application occurred via a foliar spray at the rates indicated in Tables 7 and 8, below. Table 7, below, demonstrates the yield at harvest of almond nutmeat in kilograms per hectare. Table 8, below, demonstrates the percentage of shells harvested that contained two nut kernels.

TABLE 7

| Timing of App. | Rate/App (g/Ha) | Newman | Sutter |
|---|---|---|---|
| UTC | 0 | 3090 c | 3133 b |
| Bloom | 124 | 3188 c | 3658 a |
| Shuck split | 124 | 3369 b | 3758 a |
| 7-days post shuck split | 124 | 3726 a | 3558 ab |

TABLE 8

| Timing of App. | Rate/App (g/Ha) | Newman | Sutter |
|---|---|---|---|
| UTC | 0 | 2.7 | 0.3 |
| Bloom | 124 | 2.7 | 1.2 |
| Shuck split | 124 | 2.2 | 0.7 |
| 7-days post shuck split | 124 | 3.0 | 0.5 |

Results

As seen in Table 7, above, the application of AVG to almond trees during bloom increases nutmeat yield over untreated control. Unexpectedly, treating almond trees with AVG post-bloom resulted in a greater increase in nutmeat yield than that obtained when treating during bloom. This greater increase is unexpected as the specimen label for AVG use on almonds states that application after full bloom will reduce the efficacy of the treatment. Further, as seen in Table 8, treating almond trees during bloom results in a statistically significant increase in kernel doubling in the Sutter, Calif. trial. Surprisingly, treating almond trees with AVG post-bloom did not result in a statistically significant increase in kernel doubling.

What is claimed is:

1. A method of increasing almond nutmeat yield comprising applying aminoethoxyvinylglycine (AVG) or a salt thereof at an effective rate to an almond tree wherein application occurs at least about 2 weeks following petal fall and prior to harvest and wherein the application of AVG to the almond tree does not increase the number of almond shells with two kernels as compared to an almond tree that did not receive an application of AVG.

2. The method of claim 1, wherein the effective rate is from about 1 to about 2,000 grams per hectare.

3. The method of claim 1, wherein the effective rate is from about 60 to about 1,660 grams per hectare.

4. The method of claim 1, wherein application occurs one or more times.

5. The method of claim 1, wherein application occurs once or twice.

6. The method of claim 1, wherein application occurs as a foliar spray.

7. The method of claim 1, wherein the AVG is AVG hydrochloride.

8. The method of claim 1, wherein the AVG or salt thereof is formulated with one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and preservatives.

9. A method of increasing almond nutmeat yield comprising applying aminoethoxyvinylglycine (AVG) or a salt thereof at an effective rate to an almond tree wherein application occurs at least about 7 days following shuck split and prior to harvest and wherein the application of AVG to the almond tree does not increase the number of almond shells with two kernels as compared to an almond tree that did not receive an application of AVG.

10. The method of claim 9, wherein the effective rate is from about 1 to about 2,000 grams per hectare.

11. The method of claim 9, wherein the effective rate is from about 60 to about 1,660 grams per hectare.

12. The method of claim 9, wherein application occurs as a foliar spray.

13. The method of claim 9, wherein the AVG is AVG hydrochloride.

14. The method of claim 9, wherein the AVG or salt thereof is formulated with one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and preservatives.

* * * * *